US011278520B2

(12) United States Patent
Hazan

(10) Patent No.: US 11,278,520 B2
(45) Date of Patent: Mar. 22, 2022

(54) METHOD OF PREVENTING COVID-19 INFECTION

(71) Applicant: Sabine Hazan, Ventura, CA (US)

(72) Inventor: Sabine Hazan, Ventura, CA (US)

(*) Notice: Subject to any disclaimer, the term of this patent is extended or adjusted under 35 U.S.C. 154(b) by 0 days.

(21) Appl. No.: 17/114,271

(22) Filed: Dec. 7, 2020

(65) Prior Publication Data
US 2021/0299091 A1 Sep. 30, 2021

Related U.S. Application Data

(60) Provisional application No. 63/022,368, filed on May 8, 2020, provisional application No. 63/002,494, filed on Mar. 31, 2020.

(51) Int. Cl.
*A61K 31/375* (2006.01)
*A61K 33/30* (2006.01)
*A61K 31/593* (2006.01)

(52) U.S. Cl.
CPC .......... *A61K 31/375* (2013.01); *A61K 31/593* (2013.01); *A61K 33/30* (2013.01)

(58) Field of Classification Search
CPC .................................................. A61K 31/375
See application file for complete search history.

(56) References Cited

U.S. PATENT DOCUMENTS

| | | | |
|---|---|---|---|
| 7,026,360 B1 | 4/2006 | Festo | |
| 7,351,739 B2 | 4/2008 | Ho et al. | |
| 8,178,516 B2 | 5/2012 | Shapiro | |
| 10,434,116 B2 | 10/2019 | Frieman et al. | |
| 10,987,329 B1 | 4/2021 | Raju et al. | |
| 2002/0155519 A1 | 10/2002 | Lindner et al. | |
| 2004/0071757 A1 | 4/2004 | Rolf | |
| 2005/0245502 A1 | 11/2005 | Keller | |
| 2006/0189542 A1 | 8/2006 | Furukawa et al. | |
| 2007/0026056 A1 | 2/2007 | Rolf | |
| 2007/0031510 A1 | 2/2007 | Flavin-Koenig | |
| 2012/0077786 A1 | 3/2012 | Byron et al. | |
| 2014/0147501 A1 | 5/2014 | Van Lengerich | |
| 2014/0349969 A1 | 11/2014 | Penninger et al. | |
| 2015/0309021 A1 | 10/2015 | Birnbaum et al. | |
| 2016/0015786 A1 | 1/2016 | Levesque et al. | |
| 2016/0095850 A1 | 4/2016 | Cooper et al. | |
| 2017/0189443 A1 | 7/2017 | Parsons et al. | |
| 2019/0085069 A1 | 3/2019 | Giles-Komar et al. | |
| 2020/0085737 A1 | 3/2020 | Bellinger et al. | |
| 2020/0102287 A1 | 4/2020 | Page et al. | |
| 2020/0172480 A1 | 6/2020 | Zhao et al. | |
| 2020/0237689 A1 | 7/2020 | Peralta et al. | |

FOREIGN PATENT DOCUMENTS

| | | |
|---|---|---|
| CA | 1160570 | 1/1984 |
| EP | 3513782 | 7/2019 |
| JP | 2014042514 | 3/2014 |
| WO | WO0078268 | 12/2000 |
| WO | WO2007023370 | 3/2007 |
| WO | WO2013040526 | 3/2013 |
| WO | WO2018161039 | 9/2018 |
| WO | WO2019051380 | 3/2019 |
| WO | WO2019199918 | 10/2019 |
| WO | WO2020051498 | 3/2020 |
| WO | WO2020214716 | 10/2020 |

OTHER PUBLICATIONS

Saul, A., "Vitamin C Protects Against Coronavirus", Orthormolecular Medicine News Service, Jan. 26, 2020.*
Lichtenstein, K., "Can vitamin C prevent and treat coronavirus?", Mar. 9, 2020, medicinenet.com. (printed from https://www.medicinenet.com/script/main/art.asp?articlekey=228745 on Feb. 27, 2021).*
Kearns, M. et al., "Large, single-dose, oral vitamin D supplementation in adult populations: A systematic review", Endocr Pract. Apr. 2014 ; 20 (4); 341-351.*
Dean, C. "Magnesium" Orthomolecular Medicine News Service, Nov. 9, 2017, printed from http://www.orthomolecular.org/resources/omns/v13n22.shtml on Aug. 17, 2021. (Year: 2017).*
Steinbrenner, H. et al., "Dietary selenium in adjuvant therapy of viral and bacterial infections", Adv Nutr, Jan. 15, 2015; 6(1): 73-82. (Year: 2015).*
YouTube, Italian Covid-19 Patient in Rajasthan Tests Negative After Being Treated With HIV, Swine Flu and Malaria Drugs By Swarajya Staff. Mar. 13, 2020 at 7:10 PM. https://youtu.be/IR_W4s6LoYg News Brief.
Grimwood et al. "Vaccination against respiratory pseudomonas aeruginosa infection". Hum Vaccin Immunother. 2015;11(1):14-20. doi: 10.4161/hv.34296. Epub Nov. 1, 2014.
"French researcher posts successful Covid-19 drug trial." The Connexion. Mar. 17, 2020. https://www.connexionfrance.com/French-news/French-researcher-in-Marseille-posts-successful-Covid-19-coronavirus-drug-trial-results.
Cao et al. "A Trial of Lopinavir-Ritonavir in Adults Hospitalized with Severe Covid-19." The New England Journal of Medicine. The New England Journal of Medicine, vol. 382, No. 19. May 7, 2020. https://www.nejm.org/doi/full/10.1056/NEJMoa2001282?query=featured_home.
Banjanac et al. "Anti-Inflammatory Mechanism of Action of Azithromycin in LPS-Stimulated J774A.1 Cells." Pharmacological Research, vol. 66, No. 4, 2012, pp. 357-362., doi:10.1016/j.phrs.2012.06.011.
Cortegiani et al. "A Systematic Review on the Efficacy and Safety of Chloroquine for the Treatment of COVID-19." Journal of Critical Care, 2020, doi:10.1016/j.jcrc.2020.03.005.

(Continued)

*Primary Examiner* — Gina C Justice
(74) *Attorney, Agent, or Firm* — Cislo & Thomas, LLP

(57) ABSTRACT

A method of preventing COVID-19 infection in a healthy individual, the method comprising the steps of a) providing the healthy individual; b) administering, on day 1, 10,000 mg of vitamin C, 40,000 mg of vitamin D, and 50 mg of zinc; c) administering daily, on days 2 and 3, 10,000 mg of vitamin c and 50 mg of zinc; d) administering daily, on days 4 through 7, 3,000 mg of vitamin c and 50 mg of zinc; and e) repeating steps b) and c) for 1 to 23 weeks.

4 Claims, 1 Drawing Sheet

(56) References Cited

OTHER PUBLICATIONS

Gao et al. "Breakthrough: Chloroquine Phosphate Has Shown Apparent Efficacy in Treatment of COVID-19 Associated Pneumonia in Clinical Studies." BioScience Trends, vol. 14, No. 1, 2020, pp. 72-73., doi:10.5582/bst.2020.01047.

Gautret et al. "Hydroxychloroquine and Azithromycin as a Treatment of COVID-19: Results of an Open-Label Non-Randomized Clinical Trial." International Journal of Antimicrobial Agents, 2020, p. 105949., doi:10.1016/j.jantimicag.2020.105949.

Gupta et al. "Clinical Considerations for Subjects with Diabetes in Times of COVID-19 Epidemic." Diabetes & Metabolic Syndrome: Clinical Research & Reviews, vol. 14, No. 3, 2020, pp. 211-212., doi:10.1016/j.dsx.2020.03.002.

Zhang et al. "Potential Interventions for Novel Coronavirus in China: A Systematic Review." Journal of Medical Virology, vol. 92, No. 5, 2020, pp. 479-490., doi:10.1002/jmv.25707.

PCT/US2021/023486, International Search Report and Written Opinion dated Jun. 8, 2021. 12 pages.

Ferreira C, Viana SD, Reis F. Gut Microbiota Dysbiosis-Immune Hyperresponse-Inflammation Triad in Coronavirus Disease 2019 (COVID-19): Impact of Pharmacological and Nutraceutical Approaches. Microorganisms 2020; 8(10). Oct. 2020.

Yeoh YK, Zuo T, Lui GC, et al. Gut microbiota composition reflects disease severity and dysfunctional immune responses in patients with COVID-19. Gut 2021. Jan. 2021.

Zhou F, Yu T, Du R, et al. Clinical course and risk factors for mortality of adult inpatients with COVID-19 in Wuhan, China: a retrospective cohort study. Lancet 2020; 395(10229): 1054-62. Mar. 2020.

Gasbarrini G, Dionisi T, Franceschi F, Gasbarrini A. Editorial—COVID-19 and the microbiota: new kids on the block. Eur Rev Med Pharmacol Sci 2020; 24(9): 5189-91. Jan. 2020.

Janda L, Mihalcin M, Stastna M. Is a healthy microbiome responsible for lower mortality in COVID-19? Biologia (Bratisl) 2020: 1-11. Oct. 2020.

Galeotti C, Bayry J. Autoimmune and inflammatory diseases following COVID-19. Nat Rev Rheumatol 2020; 16(8): 413-4. Jun. 2020.

Tay MZ, Poh CM, Renia L, MacAry PA, Ng LFP. The trinity of COVID-19: immunity, inflammation and intervention. Nat Rev Immunol 2020; 20(6): 363-74. Apr. 2020.

Zuo T, Zhang F, Lui GCY, et al. Alterations in Gut Microbiota of Patients With COVID-19 During Time of Hospitalization. Gastroenterology 2020; 159(3): 944-55 e8. May 2020.

Ferreira C, Viana SD, Reis F. Is Gut Microbiota Dysbiosis a Predictor of Increased Susceptibility to Poor Outcome of COVID-19 Patients? An Update. Microorganisms 2020; 9(1). Dec. 2020.

Follmer C. Gut Microbiome Imbalance and Neuroinflammation: Impact of COVID-19 on Parkinson's Disease. Mov Disord 2020; 35(9): 1495-6. Aug. 2020.

Belancic A. Gut microbiome dysbiosis and endotoxemia—Additional pathophysiological explanation for increased COVID-19 severity in obesity. Obes Med 2020; 20: 100302. Sep. 2020.

Follmer C. Viral Infection-Induced Gut Dysbiosis, Neuroinflammation, and alpha-Synuclein Aggregation: Updates and Perspectives on COVID-19 and Neurodegenerative Disorders. ACS Chem Neurosci 2020; 11(24): 4012-6. Nov. 2020.

Zuo T, Zhan H, Zhang F, et al. Alterations in Fecal Fungal Microbiome of Patients With COVID-19 During Time of Hospitalization until Discharge. Gastroenterology 2020; 159(4): 1302-10 e5. Jun. 2020.

Kim HS. Do an Altered Gut Microbiota and an Associated Leaky Gut Affect COVID-19 Severity? mBio 2021; 12(1). Jan. 2021.

Gohil K, Samson R, Dastager S, Dharne M. Probiotics in the prophylaxis of COVID-19: something is better than nothing. 3 Biotech 2021; 11(1): 1. Nov. 2020.

Ahlawat S, Asha, Sharma KK. Immunological co-ordination between gut and lungs in SARS-CoV-2 infection. Virus Res 2020; 286: 198103. Jul. 2020.

Marsland BJ, Trompette A, Gollwitzer ES. The Gut-Lung Axis in Respiratory Disease. Ann Am Thorac Soc 2015; 12 Suppl 2: S150-6. May 2015.

Antunes Aec, Vinderola G, Xavier-Santos D, Sivieri K. Potential contribution of beneficial microbes to face the COVID-19 pandemic. Food Res Int 2020; 136: 109577. 17. Jul. 2020.

Alkhater SA. Dynamic Interplay Between Microbiota and Mucosal Immunity in Early Shaping of Asthma and its Implication for the COVID-19 Pandemic. J Asthma Allergy 2020; 13: 369-83. Sep. 2020.

Penninger JM, Grant MB, Sung JJY. The Role of Angiotensin Converting Enzyme 2 in Modulating Gut Microbiota, Intestinal Inflammation, and Coronavirus Infection. Gastroenterology 2021; 160(1): 39-46. Oct. 2020.

Assante G, Williams R, Youngson NA. Is the increased risk for MAFLD patients to develop severe COVID-19 linked to perturbation of the gut-liver axis? J Hepatol 2020. Jun. 2020.

Wang F, Zheng S, Zheng C, Sun X. Attaching clinical significance to COVID-19-associated diarrhea. Life Sci 2020; 260: 118312. Aug. 2020.

Meini S, Zini C, Passaleva MT, et al. Pneumatosis intestinalis in COVID-19. BMJ Open Gastroenterol 2020; 7(1). Jun. 2020.

Carding S, Verbeke K, Vipond DT, Code BM, Owen LJ. Dysbiosis of the gut microbiota in disease. Microb Ecol Health Dis 2015; 26: 26191. Feb. 2015.

Alam MT, Amos GCA, Murphy ARJ, Murch S, Wellington EMH, Arasaradnam RP. Microbial imbalance in inflammatory bowel disease patients at different taxonomic levels. Gut Pathog 2020; 12:1. Jan. 2020.

Hegde S, Lin YM, Golovko G, et al. Microbiota dysbiosis and its pathophysiological significance in bowel obstruction. Sci Rep 2018; 8(1): 13044. Sep. 2018.

Canoui E, Ingen-Housz-Oro S, Ortonne N, et al. [Hemophagocytic lymphohistiocytosis with granulomatosis and diffuse T-cell infiltration associated with disseminated Nocardiosis and pulmonary infection due to *Streptomyces* spp]. Rev Med Interne 2019; 40(7): 457-61. May 2019.

Bolourian A, Mojtahedi Z. Streptomyces, shared microbiome member of soil and gut, as 'old friends' against colon cancer. FEMS Microbiol Ecol 2018; 94(8). Jun. 2018.

Gureev AP, Shaforostova EA, Vitkalova IY, et al. Long-term mildronate treatment increased Proteobacteria level in gut microbiome, and caused behavioral deviations and transcriptome change in liver, heart and brain of healthy mice. Toxicol Appl Pharmacol 2020; 398: 115031. Jul. 2020.

Degruttola AK, Low D, Mizoguchi A, Mizoguchi E. Current Understanding of Dysbiosis in Disease in Human and Animal Models. Inflamm Bowel Dis 2016; 22(5): 1137-50. May 2016.

Bamola VD, Ghosh A, Kapardar RK, et al. Gut microbial diversity in health and disease: experience of healthy Indian subjects, and colon carcinoma and inflammatory bowel disease patients. Microb Ecol Health Dis 2017; 28(1): 1322447. Apr. 2017.

Nayfach S, Shi ZJ, Seshadri R, Pollard KS, Kyrpides NC. New insights from uncultivated genomes of the global human gut microbiome. Nature 2019; 568(7753): 505-10. Apr. 2019.

Rizzatti G, Lopetuso LR, Gibiino G, Binda C, Gasbarrini A. Proteobacteria: A Common Factor in Human Diseases. Biomed Res Int 2017; 2017: 9351507 Nov. 2017.

Rinninella E, Raoul P, Cintoni M, et al. What is the Healthy Gut Microbiota Composition? A Changing Ecosystem across Age, Environment, Diet, and Diseases. Microorganisms 2019; 7(1). Jan. 2019.

Shin NR, Whon TW, Bae JW. Proteobacteria: microbial signature of dysbiosis in gut microbiota. Trends Biotechnol 2015; 33(9): 496-503. Jul. 2015.

Pachikian BD, Neyrinck AM, Deldicque L, et al. Changes in intestinal bifidobacteria levels are associated with the inflammatory response in magnesium-deficient mice. J Nutr 2010; 140(3): 509-14. Jan. 2010.

(56) References Cited

OTHER PUBLICATIONS

Suzuki A, Ito M, Hamaguchi T, et al. Quantification of hydrogen production by intestinal bacteria that are specifically dysregulated in Parkinson's disease. PLoS One 2018; 13(12): e0208313. Dec. 2018.

Cattaneo A, Cattane N, Galluzzi S, et al. Association of brain amyloidosis with proinflammatory gut bacterial taxa and peripheral inflammation markers in cognitively impaired elderly. Neurobiol Aging 2017; 49: 60-8. Aug. 2016.

Zaneveld JR, McMinds R, Vega Thurber R. Stress and stability: applying the Anna Karenina principle to animal microbiomes. Nat Microbiol 2017; 2: 17121. Aug. 2017.

Mortensen EM, Coley CM, Singer DE, et al. Causes of death for patients with community-acquired pneumonia results from the Pneumonia Patient Outcomes Research Team cohort study. Arch Intern Med 2002; 162(9): 1059-64. May 2002.

Alanio A, Delliere S, Fodil S, Bretagne S, Megarbane B. Prevalence of putative invasive pulmonary aspergillosis in critically ill patients with COVID-19. Lancet Respir Med 2020; 8(6): e48-e9. May 2020.

Steenwyk JL, Mead ME, de Castro PA, et al. Genomic and phenotypic analysis of COVID-19-associated pulmonary aspergillosis isolates of Aspergillus fumigatus. bioRxiv 2020. Nov. 2020.

Bruno G, Fabrizio C, Buccoliero GB. COVID-19-associated pulmonary aspergillosis: adding insult to injury. Lancet Microbe 2020; 1(3): e106. Jul. 2020.

Lescure FX, Bouadma L, Nguyen D, et al. Clinical and virological data of the first cases of COVID-19 in Europe: a case series. Lancet Infect Dis 2020; 20(6): 697-706. Mar. 2020.

* cited by examiner

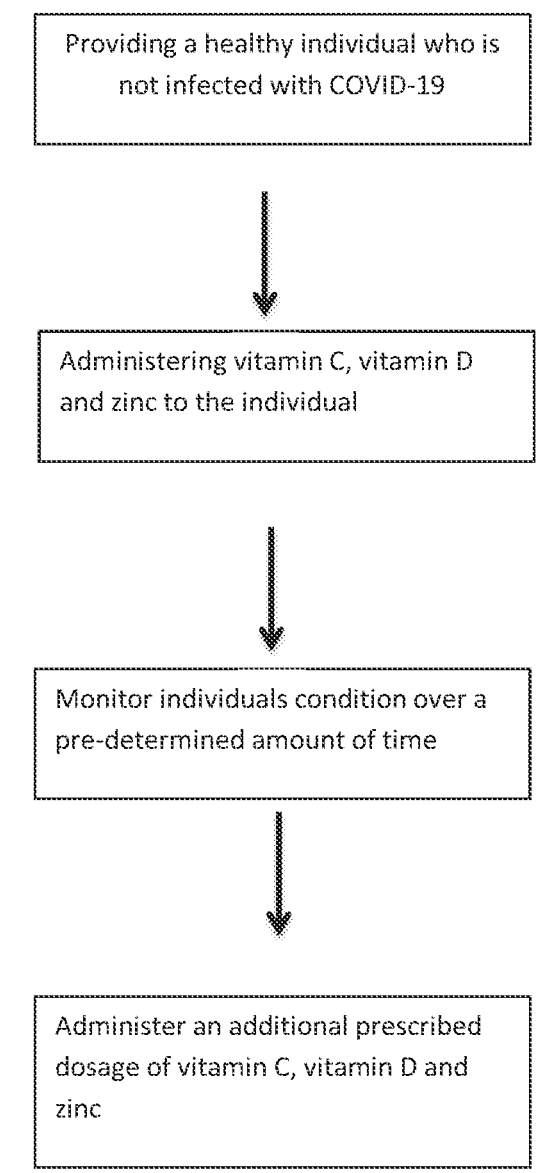

METHOD OF PREVENTING COVID-19 INFECTION

CROSS-REFERENCE TO RELATED APPLICATIONS

This application claims priority to U.S. Provisional Application Ser. No. 63/002,494, titled "Method of Using Vitamin C, Vitamin D, Zinc, and Optionally Hydroxychloroquine, to Prevent COVID-19 infection," filed Mar. 31, 2020, and also claims priority to U.S. Provisional Application Ser. No. 63/022,368, titled "Method of Using Vitamin C, Vitamin D, Zinc, and Optionally Hydroxychloroquine, to Prevent COVID-19 Infection," filed May 8, 2020, the contents of which are incorporated by reference in their entirety.

BACKGROUND

COVID-19 is a novel betacoronavirus that originated in bats in the city of Wuhan, China. This disease has rapidly spread to become a worldwide pandemic. Scientists have identified the molecular structure of the spike glycoproteins on the surface of the virus, which are what allow the virus to "stick" to its target, and in this case the human lung. The virus has a very similar sequence and structure to the coronavirus that causes SARS, with the exception of the receptor binding domain. In this domain there is a loopy, flexible glycyl in place of a rigid prolyl, which allows it to tightly bind to a hydrophobic pocket in the receptor, ACE2.

Thus, there is a significant unmet need for preventing this viral infection.

SUMMARY

The present invention addresses this need. The invention is directed to a method of preventing COVID-19 infection in a healthy individual, the method comprising the steps of:
  a) providing the healthy individual;
  b) administering, on day 1, 1,000 mg to 10,000 mg of vitamin C, 1,000 mg to 40,000 mg of vitamin D, and 25 mg to 75 mg of zinc;
  c) administering daily, on days 2 through 7, 1,000 mg to 10,000 mg of vitamin c and 25 mg to 75 mg of zinc; and
  d) repeating steps b) and c) for 1 to 23 weeks.

Optionally, step c) comprises administering daily, on days 2 and 3, 10,000 mg of vitamin c and 50 mg of zinc; and administering daily, on days 4 through 7, 3,000 mg of vitamin c and 50 mg of zinc.

Optionally, step c comprises assessing the patient for potential adverse events, serious adverse events, and COVID-19 symptoms.

Optionally, steps b) and c) comprise administering selenium, copper and other vitamins that are appropriate supplements for vitamin C, vitamin D or zinc.

DRAWINGS

These and other features, aspects and advantages of the present invention will be better understood with reference to the following description, appended claims, and accompanying drawings where:

FIG. 1 is a flow chart depicting the steps of a first method of preventing infection with COVID-19.

DETAILED DESCRIPTION OF THE INVENTION

The following discussion describes in detail one embodiment of the invention with several variations of that embodiment. This discussion should not be construed, however, as limiting the invention to those particular embodiments. Practitioners skilled in the art will recognize numerous other embodiments as well.

This invention describes a method of triple therapy for preventing a COVID-19 infection.

Definitions

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

As used in this disclosure, the term "comprise" and variations of the term, such as "comprising" and "comprises," are not intended to exclude other additives, components, integers, ingredients or steps.

The present invention is directed to a method of preventing COVID-19 infection in an individual. The method comprises administering three different supplements. The supplements comprise:

Vitamin C, Vitamin D, Zinc, and any mixtures thereof.

The length of preventative treatment of the present invention can be as long as necessary. However, regardless of the length of treatment, Vitamin C is provided at 10,000 mg daily for the first three days of treatment, and then 3000 mg daily thereafter. This 10,000 mg of Vitamin C can be broken up into two doses, one taken in the morning and one taken at night.

Vitamin D is provided at 40,000 mg one day every 4 weeks (or however many weeks the preventative treatment lasts). This 40,000 mg of Vitamin D can be broken up into two doses, one taken in the morning and one taken at night.

Zinc is provided at 50 mg per day ongoing, for the length of the preventative treatment. This 50 mg of Zinc can be broken up into two doses, one taken in the morning and one taken at night.

On Day 1 (Week 1), the patient provides verbal informed consent, the patient reviews prior (previous 3 months) and concomitant medications and the patient receives the three different supplements: Vitamin C, Vitamin D, and Zinc. The patient takes 10,000 mg of Vitamin C, 40,000 mg of Vitamin D, and 50 mg of zinc.

On Days 2 and 3 (Week 1), the patient takes 10,000 mg of Vitamin C and 50 mg of zinc daily. This 3,000 mg can be broken up into two 1500 mg doses, one taken in the morning and one taken at night. The patient is called on the phone for assessment for potential adverse events (AE) and serious adverse events (SAE), and any COVID-19 symptoms.

On Days 4-7 (Week 1), the patient takes 3,000 mg of Vitamin C and 50 mg of zinc daily.

On Day 8 (Week 2), the patient takes 3,000 mg of Vitamin C, 40,000 mg of Vitamin D, and 50 mg of zinc.

On Days 9-14 (Week 2), the patient takes 3,000 mg of Vitamin C and 50 mg of zinc daily.

Weeks 3-24 continue with the same protocol identified above for Week 2.

During Weeks 1-23, the patient is called weekly on the phone for assessment for adverse events and serious adverse events, and any COVID-19 symptoms. The list of prior and concomitant medications is also updated.

During Week 24, the patient is called to the clinic for evaluation to include assessment for potential adverse events and serious adverse events, to update the list of prior and concomitant medications, to perform confirmatory COVED-19 testing, and to perform blood testing.

Optionally, Vitamin C dosage can range from 1000 mg to 10,000 mg per day, Vitamin D dosage can range from 1000 IU to 40000 IU per day, Zinc (the zinc can be any type or form of zinc) dosage can range from 25-75 mg per day. As noted above, all daily doses of Vitamin C, Vitamin D and Zinc can be broken up into two daily doses, wherein one dose is taken in the morning and one dose is taken in the evening. For all protocols provided in this application, when a dosage range is provided, any dosage amount that is included in that range can be administered. Accordingly, the invention is not limited to the dosage ranges disclosed, and includes all dosage amounts contained in those ranges.

The protocol provided in this application can also include selenium, copper and other vitamins that are deemed appropriate supplements for Vitamin C, Vitamin D or Zinc or, to counteract the negative depletion of certain vitamins, like copper or selenium.

Treatment can be for one day or consecutive or repeated in 2 weeks, 1 month, 6 months or 1 year.

The Vitamin C, Vitamin D and Zinc, and mixtures thereof, can be administered orally, in the form pills/lozenges, an aerosolized spray, or a food substance such as a liquid drink or yogurt composition. Optionally, the Vitamin C, Vitamin D and Zinc can be administered in the form of a nasal spray or a topical application, such a lotion or spray for administration on the individual's skin.

Table 1 outlines the schedule of events for this protocol.

a. Vitals to include height (only at first visit), weight, blood pressure (following 5 minutes sitting), pulse, respiratory rate, temperature, and oxygen saturation.

b. Future testing will require separate informed consent and can include antibody or cytokine testing.

COVID-19 sample collection period (to be conducted by patient's physician if infection is suspected at any time during the study or after). Nasopharyngeal (NP) and oropharyngeal (OP) swabs will be collected according to CDC protocol—which include synthetic fiber swabs with plastic shafts. The NP swabs are collected by insertion of a swab into the nostril parallel to the palate. The swab is left in place a few seconds to allow it to absorb secretions. The OP swabs are inserted into the oropharynx parallel to the palate, avoiding the tongue. The swab is left in place a few seconds to allow it to absorb secretions. These swabs are immediately placed in sterile tubes with 2-3 mL of viral transport media. The tubes are placed in biohazard bags then boxes and couriered to the local Public Health Lab.

The above protocols can be used to prevent infection with other viruses (not just COVID-19), including other flu viruses.

The above protocols can also be used to treat Autism, Parkinson's, Alzheimer's and other neurological diseases.

EXAMPLES

Example 1

Successful Treatment of COVID-19 Infected Outpatients and Prophylaxis of Immediate Associates Objective: to successfully treat COVID-19 infected outpatients and prophylaxis of immediate associates.

Procedure: Prospective COVID-19 infected individuals were diagnosed using a Pangea DNA/RNA Shield Collection Tube to obtain a nasopharyngeal swab and PCR +ve patients were entered into the study. They were immediately commenced on a 10 day course of Hydroxychloroquine (200 mg, twice a day, for 10 days), Azithromycin extended release (500 mg on day 1, then 250 mg a day for days 9-10), zinc (50 mg a day for days 1-10), Vitamin D (3000 IU) a day for days 1-10) and Vitamin C (3000 mg, a day for days 1-10). Some individuals lived alone, otherwise immediate partners and family deemed to be most exposed were given a prophylactic which comprised hydroxychloroquine 200 mg twice a day on day 1 only with Zinc, Vitamin C and Vitamin D for given at the same doses as above for days 1-10.

TABLE 1

| Assessment | Screening (Day 1) | Day 2 | Day 3 | Day 4 | Weeks 1-23 | Week 24/ET (14 d) |
|---|---|---|---|---|---|---|
| Informed Consent & Demographics | X | | | | | |
| Review of Prior and Concomitant Medications | X | | | | | |
| Physical Exam | | | | | | X |
| Vitals[a] | | | | | | X |
| Prescription of vitamin C, vitamin D, and zinc | X | | | | | |
| Update list of prior and concomitant medications | X | | | | X | X |
| Ask about AE and SAE | | X | X | | X | X |
| Update dose of Vitamin C to 3000 mg daily | | | | X | | |
| Evaluation for COVID-19 symptoms | | | | | X | X |
| COVID-19 testing | | | | | | X |
| a. Blood draw for future testing[b] | | | | | | X |

Results: In 11 families a total of 21 family members were identified to be PCR COVID-19 positive index cases and were treated with the above treatment protocol while 22 exposed associates with negative PCR were given the above prophylaxis protocol. This is shown below in Table 24. All 21 index cases were cured of COVID-19 infection as judged by the repeat swab PCR on day 10 and accompanying symptom resolution. None of the 22 highly exposed associates developed COVID-19 infection when retested on day 10 (day 14 in Family 10) in spite of close co-habitation with the infected index cases, TABLE 2: Results from families received 10-day course of daily HCQ (200 mg bd), AZ extended release (500 mg day 1, then 250 mg), zinc (50 mg), Vitamin D (3000 IU) and Vitamin C (3000 mg)

TABLE 2

| Family | Patient/s treated | Age (years)- sex of the patient | Comorbidities of the patients | After treating with HAZDPAC Cured/ PCR test positive/negative/ other symptoms | After treating ZINCD + H family member prophylaxed |
|---|---|---|---|---|---|
| #1 | 1 | 23 - male | Asthma | Negative PCR - day 10 | Parents overweight, diabetes, father with heart disease never got the disease |
| #2 | 3 | 60- male (father) 18- male (son) 16- female (daughter) | Asthma | All 3 patients cured | Mother didn't get the virus |
| #3 | 1 | 40-female | Avoided intubation by leaving hospital | Sever multiple symptoms resolved at home | Husband did not turn positive |
| #4 | 2 | 78- male 77- female | BCG + COPD, diabetes, heart disease (heart surgery month prior Pacemaker, BCG | Both cured | Daughter, son-in-law and 2 grandkids didn't catch the virus |
| #5 | 3 | 56-male 27- male 24- female | Unable to eat or drink Asthma | Started treatment on day 10, Sever symptoms resolved Cured | Wife never got the disease |
| #6 | 1 | 56- female |  | Admitted to hospital-sent home, as two kids were sick with fever. All recovered with vitamins | Husband never got the disease |
| #7 | 1 | 44-female |  | Cured, autoimmune issues started | Husband and 4 kids never got the disease |
| #8 | 3 | 52- female 53- male 19- male | Lupus Severe asthma | Cured Cured Cured | Boyfriend (54 y) with Diabetes, son (18) and daughter (16) never got. the disease |
| #9 | 2 | 45-female 16-male |  | Both cured from severe symptoms of cough and fever | Husband and daughter never got the disease |
| #10 | 2 | 44- male 25- female 21-female |  | Cured from loss of smell, fever, cough Cured Partially treated with HAZDPAC - slowly turned –ve | Mother (50 y) never got the disease |
| #11 | 1 | 33-female | No | ICU nurse recovered | Boyfriend never got the disease |

Apart from the families a further 11 single infected individuals found to be swab PCR positive were treated with the above treatment protocol. This is shown below in Table 3. All were also successfully cured of the infection.

TABLE 3

| Patient | Age (years)- sex of the patient | Comorbidities/symptoms of the patients | After treating with HAZDPAC Cured/not |
|---|---|---|---|
| #1 | 44-female (no BCG in childhood) | Asthma | Cured |
| #2 | 81- male | Diarrhea | Cured |
| #3 | 52-female | Fever | Cured |
| #4 | 66-male | Valve surgery | Cured |
| #5 | 29-female (no BCG | Asthma | Cured |

TABLE 3-continued

| Patient | Age (years)- sex of the patient | Comorbidities/symptoms of the patients | After treating with HAZDPAC Cured/not |
|---|---|---|---|
| | in childhood) | | |
| #6 | 50-female | Auto immune thyroiditis, sever cough and fever | Cured |
| #7 | 43-male | Cough, desaturation of oxygen | Cured |
| #8 | 53-male | Diarrhea, cough, fever, desaturation of oxygen | Cured |
| #9 | 44- female | Autoimmune history, fever, increase heart rate | Cured |
| #10 | 44- female | Pneumothorax discharged from ICU with COVID-19 | Cured |
| #11 | 43- male | Fever +ve Covid-19 PCR | Cured |

A further 9 individuals recently closely exposed to Covid-19 infected persons were given the prophylaxis protocol outlined above. The prophylactic worked very well with no exposed person acquiring the infection. This is shown in Table 4.

TABLE 4

| Individual | Age (years) & details of the individual | After treating with ZINCD + H |
|---|---|---|
| #1 | Mother of 16 year old child who had COVID-19 | Prophylaxed and never got the disease |
| #2 | 24- female, ICU nurse - multiple exposures | Prophylaxed and never got the disease |
| #3 | 47- male, cardiologist exposed to +ve patients | Prophylaxed and never got the disease |
| #4 | 70- male medical director of a hospital (exposed to numerous doctors with COVID-19) | Prophylaxed and never got the disease |
| #5 | 55- male anaesthesiologist (intubates COVID-19 patients) | Prophylaxed and never got the disease |
| #6 | 55- ICU nurse (worked on COVID-19 floor) | Prophylaxed and never got the disease |
| #7 | 40- ICU nurse many Covid-19 patients | Prophylaxed and never got the disease |
| #8 | 53-Doctor with pancreatitis | Prophylaxed and never got the disease |
| #9 | 28-Paramedic - healthy | Prophylaxed and never got the disease |

Discussion: it was demonstrated that a 10 day combination of hydroxychloroquine, azithromycin (for 5 days only), zinc with vitamin D and vitamin C, can result in uniform cure of COVID-19 infection when used in an outpatient population. The prophylaxis treatment noted above for those closely exposed to proven, infected patients can completely prevent spread of COVID-19. This combination of test-and-treat permits abolishing of new outbreaks of infection such as a 'next wave'—by avoiding quarantine to treat the infected and give prophylactics to surrounding staff and family.

In conclusion, this is an effective anti-Covid-19 therapy as well as an effective prophylactic combination capable of arresting the spread of coronavirus infection throughout the community. This is achieved by treating the index case and the surrounding associates of the patient as early as possible after infection is identified and then treating the people they live with and close associates.

Having thus described the invention, it should be apparent that numerous structural modifications and adaptations may be resorted to without departing from the scope and fair meaning of the instant invention as set forth herein above and described herein below by the claims.

What is claimed is:

1. A method of preventing COVID-19 infection in a healthy individual, the method consisting of the steps of:
   a) providing the healthy individual;
   b) administering, on day 1:
      i) 10,000 mg of vitamin C;
      ii) 40,000 IU of vitamin D; and
      iii) 50 mg of zinc;
   c) administering daily, on days 2 and 3:
      i) 10,000 mg of vitamin c; and
      ii) 50 mg of zinc;
   d) administering daily, on days 4 through 7:
      i) 3,000 mg of vitamin c; and
      ii) 50 mg of zinc; and
   e) repeating steps b) and c) for 1 to 23 weeks.

2. A method of preventing COVID-19 infection in a healthy individual, the method consisting of the steps of:
   a) providing the healthy individual;
   b) administering, on day 1, 1,000 mg to 10,000 mg of vitamin C, 1,000 IU to 40,000 IU of vitamin D, and 25 mg to 75 mg of zinc;
   c) administering daily, on days 2 through 7, 1,000 mg to 10,000 mg of vitamin c and 25 mg to 75 mg of zinc; and
   d) repeating steps b) and c) for 1 to 23 weeks.

3. The method of claim 2, wherein step c) comprises:
   a) administering daily, on days 2 and 3, 10,000 mg of vitamin c and 50 mg of zinc; and
   b) administering daily, on days 4 through 7, 3,000 mg of vitamin c and 50 mg of zinc.

4. A method of preventing COVID-19 infection in a healthy individual, the method consisting of the steps of:
   a) providing the healthy individual;
   b) administering, on day 1:
      i) 10,000 mg of vitamin C;
      ii) 40,000 IU of vitamin D; and
      iii) 50 mg of zinc;
   c) administering daily, on days 2 and 3:
      i) 10,000 mg of vitamin c; and
      ii) 50 mg of zinc;
   d) administering daily, on days 4 through 7:
      i) 3,000 mg of vitamin c; and
      ii) 50 mg of zinc; and
   e) repeating steps b) and c) for 1 to 23 weeks.

* * * * *